United States Patent [19]
Sagen

[11] Patent Number: 5,935,606
[45] Date of Patent: Aug. 10, 1999

[54] REVERSING EXCITOTOXIC CNS DAMAGE BY CELLULAR IMPLANTATION

[76] Inventor: Jaqueline Sagen, 2509 W. Farwell, Chicago, Ill. 60645

[21] Appl. No.: 08/509,522

[22] Filed: Jul. 31, 1995

[51] Int. Cl.[6] .................................................. A61K 35/55
[52] U.S. Cl. ........................................... 424/562; 424/93.7
[58] Field of Search ........................ 435/240.2; 424/93.1, 424/93.7, 562, 523

[56] References Cited

U.S. PATENT DOCUMENTS

| | | | |
|---|---|---|---|
| 4,806,543 | 2/1989 | Choi | 514/464 |
| 4,883,666 | 11/1989 | Sabel et al. | 424/422 |
| 5,093,525 | 3/1992 | Weber et al. | 564/238 |

OTHER PUBLICATIONS

Siegan et al., Brain Research 680(1–2): 88–98 (May 22, 1995).

The Merck Manual of Diagnosis and Therapy, 1990 pp. 1404, 1495, 1513.

Backlund et al. 1985. Transplantation of Adrenal Medullary Tissue to Striatum in Parkinsonism. In: Neural Grafting in the Mammalian CNS (Bjorklund and Stenevi, eds.). Elsevier Science Publishers pp. 551–556.

Sagen et al. 1986 Adrenal Medullary Tissue Transplants in the Rat Spinal Cord Reduce Pain Sensitivity. Brain Research; 384. pp. 189–184.

Freed et al. 1981 Transplanted adrenal chromaffin cells in rat brain reduce lesian–induced rotational behavior Nature: 292. pp. 351–352.

Patel et al. 1995. Pharmacotherapy of Cognitive Impairment in Alzheimer's Disease: A review. Journal of Geriatric Psychiatry and Neurology: 8 pp. 81–95.

*Primary Examiner*—Jean C. Witz
*Attorney, Agent, or Firm*—Rockey, Milnamow & Katz, Ltd.

[57] ABSTRACT

The use of certain types of CNS transplants in preventing and reversing excitotoxic CNS damage.

6 Claims, 12 Drawing Sheets

REVERSING EXCITOTOXIC CNS DAMAGE BY CELLULAR IMPLANTATION

BACKGROUND OF THE INVENTION

1. Technical Field

The present invention relates to a method of preventing and reversing excitatory amino acid (EAA) initiated excitotoxicity in the central nervous system and the clinical uses thereof.

2. Description of the Prior Art

The central nervous system (CNS) is comprised of the spinal cord, brain and retina, and contains trillions of nerve cells (neurons) that form networks capable of performing extremely complex functions. The key to the operation of these complex networks is the ability of neurons to communicate with each other. One of the ways neurons communicate with one another is by using neurotransmitters. Neurotransmitters are typically excitatory or inhibitory in nature. One class of the excitatory neurotransmitters is of particular interest.

Excitatory amino acids (EAAs) mediate a substantial portion of the chemical synaptic activity occurring in the CNS. However, several EAAs, like glutamate for example, which function under normal and healthy conditions as an important excitatory neurotransmitter in the CNS, can exert neurotoxic properties referred to as "excitotoxicity" if certain conditions arise.

It has long been recognized that excitatory amino acids may be neurotoxic [Lucas and Newhouse, Arch. Ophtalmol., 58:193 (1957); Olney et al, Exp. Brain Res., 14:61 (1971); Coyle et al., Neurosci. Res. Prog. Bull., 19:331 (1981)]. Prolonged exposure of cerebral neurons to high concentrations of L-glutamate or related amino acids leads to their death and degeneration [D. W. Choi, Neuron, 1:623–634, (1988); J. W. Olney, Science, 164:719–721, (1969)]. In early studies of this phenomenon, Olney showed that the neurotoxic properties of acidic amino acids were related to their ability to depolarize and excite central neurons, and the term "excitotoxicity" was coined to describe this form of activity-dependent neuronal damage. It has been suggested that these so-called "excitotoxins" may contribute to tissue damage within the central nervous system in a variety of disorders including epilepsy, neurodegenerative diseases and cerebral ischemia [B. Meldrum, Clin. Sci., 68:113 (1985); M. Pisa et al., Brain Res., 200(2):481–7 (1980)].

Current understanding recognizes at least three major ionotropic receptors for EAAs. Most commonly identified by prototypical agonists, these include: 1) receptors activated by AMPA, a cyclic analog of L-glutamate (GLU), 2) receptors activated by the neurotoxin kainic acid (KA), and 3) receptors responding to N-methyl-D-aspartate (NMDA), a synthetic analog of L-aspartate [D. R. Curtus at el., Brain Res., 41, 283–301 (1972); J. C. Watkins and R. H. Evans, Ann. Rev. Pharmacol. Toxicol., 21, 165–204 (1981); A. C. Foster and G. Fragg, Brain Res. Rev., 7, 103–164 (1984)]. In addition, evidence now suggests the presence of metabotropic EAA receptors which directly activate second messenger systems [D. Schoepp, J. Brockart and F. Sladeczek, In C. Lodge and G. L. Collinridge (eds.) Tr. Pharmacol. Sci., Special Report, "The Pharmacology of Excitatory Amino Acids," Elsevier, Cambridge, UK, p 74–81 (1991)]. Furthermore, it is also now apparent that the NMDA-mediated ionotropic receptors are subject to complex regulatory influences and, that this particular recognition site may exist as a supramolecular entity similar to the GABA/benzodiazepine/barbiturate effector proteins [E. Costa, Neuropsychopharmacology, 2, 167–174 (1989)].

In general, EAA agonists are potent convulsants. Additionally, AMPA, KA and the endogenous NMDA agonist, quinolinic acid (QA) and the mixed ionotropic/metabotropic agonist ibotenic acid have been used to produce laboratory models of neurodegenerative disorders [K. Biziere et al. In H. Yoshida, Y. Hagihara and S. Ebashi (eds.), "Advances in Pharmacology and Therapeutics," New York: Pergamon, 1982, 271–276; R. Schwarcz, E. O. Whetsell and R. M. Mango, Science, 219, 316–318 (1983)]. As mentioned above, it has also been suggested that dysfunctions in EAA neurotransmission may contribute to the neuropathologies associated with the epilepsies and neurodegenerative conditions [B. Meldrum and M. Willams (eds.), "Current and Future Trends in Anticonvulsant, Anxiety and Stroke Therapy," New York: Wiley Liss, 1990].

Dysfunction between the excitatory and inhibitory amino acids have also been implicated in the induction of the neurodegenerative process observed in motor neurons diseases (MND) such as in amyotrophic lateral sclerosis (ALS) [V. O. Gardner et al., Spine, 15:858–863 (1990)]. ALS is characterized clinically by progressive weakness and wasting of muscles caused by a slow loss of large and small neurons, predominantly motor neurons, in the ventral spinal cord, brainstem, and motor cortex. Previous studies have established that this disease is associated with increased glutamate concentrations in the CNS as well as a loss of high-affinity glutamate transport in certain brain regions and the spinal cord of affected patients [J. D. Rothstein et al., Ann. Neurol., 28:18–25 (1990); A. Plaitakis et al., Ann. Neurol., 24:446–449 (1988); J. D. Rothstein et al., N. Engl. J. Med., 236:1464–1468 (1992)]. These results suggest that the defect in glutamate transport is responsible for the sustained elevations in extracellular glutamate, which in turn would result in the injury of nearby neurons. In support for this, in ALS patients, NMDA receptor binding is reduced in the ventral horn (and also the dorsal horn) of the spinal cord, presumably due to receptor down-regulation or excitotoxic degeneration of receptor-bearing cells [C. Krieger et al., Neurosci Lett., 159:191–194 (1993); P. J. Shaw et al., Brain Res., 637:297–302 (1994)].

The development of selective EAA antagonists has further expanded the understanding of EAA neurotransmission and the resulting physiology and pathophysiology in the mammalian brain. In particular, it has been shown that NNIDA receptor antagonists possess neuroprotective properties and can alter the course of excitotoxic degeneration [I. Massieu et al., Neuroscience, 55:883–892 (1993)]. Substantial preclinical evidence is now available suggesting that NMDA receptor antagonists may be useful as anxiolytics, anticonvulsants, antiemetics [European Patent Application No. 432,994], antipsychotics or muscle relaxants, and that these compounds may prevent or reduce neuronal damage in instances of cerebral ischemia, hypoxia, hypoglycemia or trauma [R. P. Simon et al., Science, 226:850–852 (1984); D. N. Stephens et al., Psycopharmacology, 90:166–169 (1986); D. Lodge and G. L. Collingridge (eds.) "The Pharmacology of Excitatory Amino Acids," Elsevier Trends Journals, Cambridge, UK. (1991); A. J. Faden et al., Eur. J. Pharmacol., 175:165–174 (1990)]. Likewise, it has been shown that motor neuron toxicity was selectively prevented by non-NMDA glutamate receptor antagonists in models of ALS and other MND which are associated with slow neurotoxicity [J. D. Rothstein et al., Proc. Natl. Acad. Sci., 90:6591–6595 (1993)]. Excitatory amino acid antagonists have also been shown to have an analgesic effect. An initial report by Cahusac et al. indicated that intrathecal (i.t.) injection of APV, a selective NMDA antagonist, produced antinociceptive effects in tail-flick, hot-plate and paw pressure tests [P. M. B. Cahusac, R. H. Hill et al, Neuropharmacology, 23:719–724 (1984)].

Unfortunately, the levels of EAA antagonists necessary to produce the desired effects can be quite high. For example, Cahusac et al. observed that i.t. doses between 12 and 48 μg induced motor dysfunction including paralysis, while doses as high as 500 μg have been used in studies of the antinociceptive effects of APV in persistent nociceptive models [P. M. B. Cahusac, R. H. Hill et al, Neuropharmacology, 23:719–724 (1984); T. J. Coderre and I. Van Empel, Pain, 59:345–352 (1994)]. Furthermore, competitive NMDA antagonists such as APV do not cross the blood-brain barrier so clinical administration is limited, and non-competitive NMDA antagonists such as ketamine, PCP and MK-801 produce psycomotor effects at the higher dose levels and may have a limited effective dose range.

The adrenal medulla is composed of chromaffin cells supported by connective tissue elements and profusely supplied by nerves and blood vessels. Ganglion cells are present but are usually difficult to find in routine sections. Chromaffin cells are derived from neuroectoderm and were generally thought to release catecholainines (epinephrine and norepinephrine). In recent years, however, it has been discovered that chromaffin cells release many different neuroactive substances. Using antisera against chromogranins A, B, and C and neuropeptide Y, it was demonstrated that these antigens are costored with chromaffin vesicles. [Steiner, Schimid, Fisher-Colbrie et al., Histochemistry, 91:473–477 (1989)]. In a series of papers, Boinmer and Herz reported that [Met]- and [Leu]enkephalin are released together with catecholamines from cultured bovine adrenal chromaffin cells [M. Bommer and A. Herz, Life Sci., 44:327–335, (1989); M. Bommer and A. Herz, Neuropeptides, 13:243–251 (1989)]. Furthermore, chromaffin cells have been shown to release a variety of trophic factors as well. In fact, Unsicker described the release of substances from chroinaffin cells as a "trophic cocktail" [Unsicker et al., Exp. Neuro., 123:167–173 (1993)]. As a result, adrenal medullary cells have been used in attempts to treat Parkinson's disease, Chronic Pain, and to stimulate and promote the survival of other peripheral and CNS neurons.

However, adrenal chromaffin cells are not the only type of tissue to be used in neural transplantation. Both fetal and adult striatal, cortical and tectal cells have been used as well. Furthermore, reports of cross-species (xenograft) implants are also common place in the technical literature. Also, genetically altered cells, such as nerve growth factor (NGF) producing fibroblasts, have been used as a source of graft material.

Much of the literature in the field of neurotransplantation pertains to the ability of grafted material to survive in the host. With allografts, the problem of cell survival can usually be dealt with using an immunosuppressant, such as Cyclosporin A. However, attempts at cross-species transplantation have shown that such simple solutions are not adequate. Many different methods of promoting cross-species graft survivability have been demonstrated. One such method involved surrounding the graft in a polymer capsule [P. Aebischer et al., Exp. Neurol., 126:151–8 (1994); J. M. Joseph et al., Cell Transplant., 3(5):355–64 (1994)]. Others involve supplying the graft with growth factors by co-grafting the implant with another cell type which releases the 'necessary' growth factors in vivo [G. Bing et al, Brain Res. Bull., 20:399–406 (1988); J. Kordower et al., J. Neurosurg., 73:418–428 (1990)]. Finally, it has also been established that certain cell types can survive in the CNS following short-term courses of immunosuppression if isolated from their native support cells (ie., fibroblasts and endothelial cells) [J. Ortega et al., Cell Transplant., 1:33–41 (1992); S. Schueler et al., Cell Transplant., 4(1):55–64 (1995)].

Perhaps the most fundamental question which remains concerns the mechanisms of action which underlie behavioral and morphological recovery. One of the most comprehensive perspectives is in a review by Sanberg et al. [P. R. Sanberg et al., Cell Transplantation, 1(6):401–427 (1992)]. They described five alternative mechanisms of graft function which are characterized by increasingly more complex forms of host-graft interaction.

1) Nonspecific or negative consequences of the transplantation procedure. 2) Trophic actions on the host brain. Transplanted tissue may serve as a trophic support structure which exerts its behavioral protection by promoting regeneration or minimizing the extent of secondary cell loss. For example, Sanberg et al. described the use of polymer encapsulated bovine chromaffin cells (BAC) to prevent quinolinic acid induced lesions of the striatum. In their experiment, they implanted chromaffin cells into the striatum of rats as a prophylactic measure. They then tried to induce neurodegeneration by injecting quinolinic acid (QA), an endogenous EAA agonist, into the striatum. The results of this experiment was that the animals which received BAC implants showed little neuronal loss after the injection of QA, presumably due to the release of trophic factors [P. R. Sanberg et al., Soc. Neurosci. Abstr., 17:903 (1991)]. As another example, Frim et al. conducted an experiment using a genetically altered fibroblast cell line. Here, they compared that ability of NGF (nerve growth factor, a trophic factor) producing fibroblasts vs. control fibroblasts to protect against subsequent injection of an NMDA-receptor agonist. The results again were that the NGF producing fibroblasts prevented the damage caused by the excitotoxin [D. M. Frim et al., Neuroreport, 4(6):655–8 (1993)]. 3) Diffuse release of hormones or nuerotransmitters. A generalized release of nonspecific neurotransmitters or hormones into the damaged region could likely play a role in mediating recovery in several models. For example, Winnie, Sagen and Pappas have been using the fact that adrenal medullary tissue releases catecholamines and met-enkephalin to treat pain in cancer patients [Winnie et al., Anesthesiology, 79(4):644–53 (1993)]. Likewise, Aebischer and co-workers have been using dopamine-secreting PC12 cells in promoting recovery in models of Parkinson's Disease [P. Aebischer et al., Exp. Neurol. 111 :269–275 (1991); P. Aebischer et al., Biomaterials, 12:50–56 (1991)]. 4) Reinnervation of host tissue by the transplant. Reinnervation of host tissue has been suggested to underlie recovery in a variety of model systems by providing a tonic, unregulated release of neurotransmitters. Indeed, grafted tissue is capable of innervating large regions of the host brain, and in some cases results in a pattern of innervation which is remarkably similar to that normally observed. For example, Sanberg et al. examined the use of fetal striatal tissue to reverse the effects of a excitotoxin induced lesions as a model for Huntington's disease. In a series of experiments they concluded that the transplants not only had similar pharmacological properties but also a continuing functional interaction between the host brain and transplanted tissue which was a vital element in the success of the fetal striatal transplants [A. B. Norman et al., Neuropharmacology, 27(3):333–6 (1988); P. R. Sanberg et al., J. Neural Transplant., 1(1):23–31 (1989)]. 5) Establishment of reciprocal graft-host anatomical connections. Complex behaviors with requirements for both afferent and efferent circuitry would not be modified by grafted tissue which reinnervated the host tissue but did not receive reciprocal connections itself. In general, the innervation of grafted tissue by host afferents is poor and not observed very often.

However, the use of chromaffin cells or any other living cells in a method of providing EAA antagonists into the CNS has not heretofore been attempted. Nor has the use of living cells or tissue which secrete EAA antagonists to treat dysfunctions in EAA neurotransmission heretofore been attempted. Furthermore, the use of transplants which act as EAA antagonists to reverse neurodegeneration caused by EAAs has also not been previously attempted. Finally, the ability of living cells to secrete EAA antagonists in quantities sufficient to produce neuroprotective and neuroregenerative effects without also causing locomotor abnormalities yields new and surprising results not suggested in the prior art.

SUMMARY OF INVENTION

In accordance with this invention, it has been found that chromaffin cells implanted into the CNS can release substances which act as EAA antagonists. By providing the CNS with EAA antagonists, the implanted cells can thereby prevent and reverse the sequel of events which will ultimately lead to neural death and degeneration. Furthermore, by providing the CNS with a renewable supply of EAA antagonists from living cells, it will be possible to treat neurological diseases which are the result of a dysfunction in EAA neurotransmission.

It is therefore, an object of the present invention to provide a method of administering EAA antagonists into the CNS by transplanting into the CNS living cells which secrete substances which produce an EAA antagonistic effect.

It is a further object of the present invention to provide a method of treating diseases which are the result of a dysfunction in EAA deurotransmission by implanting into the CNS cells which secrete substances which produce an EAA antagonistic effect.

Other objects and advantages will become evident as the detailed description of the invention proceeds.

BRIEF DESCRIPTION OF DRAWINGS

These and other objects, features and many of the attendant advantages of the invention will be better understood upon a reading of the following detailed description when considered in connection with the accompanying drawings wherein:

FIG. 10: Light photomicrographs of spinal dorsal horn immunoreacted for the NMDA receptor NMDAR1 subunit.

FIG. 11: Light photomicrographs of spinal ventral horn immunoreacted for the NMDAR1 subunit.

Figure 1:
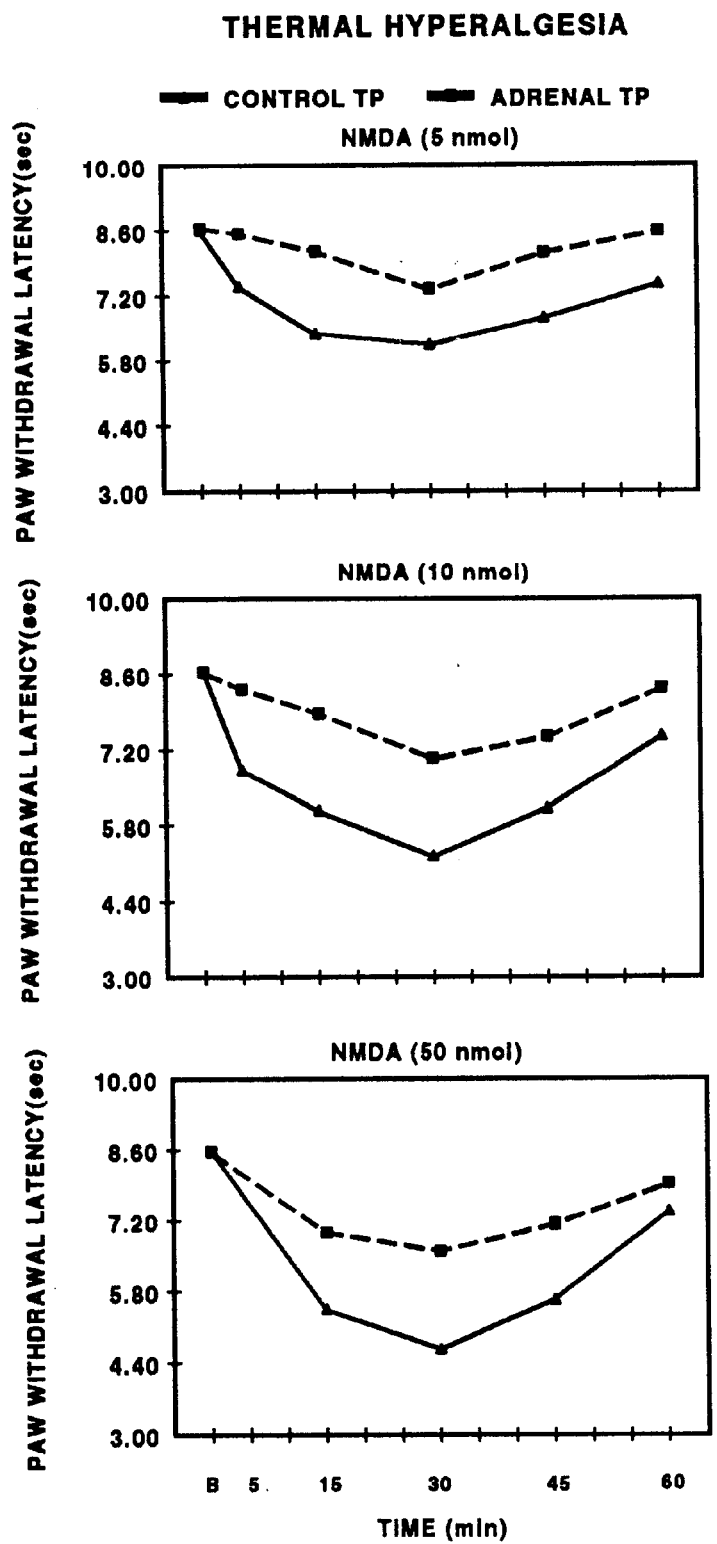
FIG. 1: Time course of thermal hyperalgesia induced by 5 nmol (top panel), 10 nmol (middle panel) and 50 nmol (lower panel) NMDA injected intrathecally in rats with adrenal medullary (squares) and control striated muscle (triangles) transplants in the spinal subarachnoid space. The ordinate is the latency to paw withdrawal response (sec) to a noxious thermal stimulus. The abscissa is time (min) after intrathecal NMDA injection. B (baseline) indicates withdrawal latencies prior to NMDA injection. All data is presented as mean+/−S.E.M., although standard errors bars were small and thus masked by the computer generated symbols. N=10 animals per group.

All data is presented as mean+/−S.E.M. (n=12 animals/group).

DETAILED DESCRIPTION OF THE INVENTION

The above and other objects and advantages of the present invention are achieved by a novel method of administering excitatory amino acid antagonists into the CNS by implanting adrenal chromaffin cells. Of course, any suitable type of living cells or tissue can be employed so long as such material is transplantable into the CNS without rejection and is capable of releasing effective amounts of substances which can provide an EAA antagonistic effect.

Chromaffin cells have long been thought to secrete primarily catacholamines. Recently, however, chromaffin cells have been shown to secrete many different types of substances. Not long ago, we generated data to show that chromaffin cells also release substances which have an antagonistic effect to EAAs. We have also generated data that establishes the implants ability to reverse pathologic changes which result from EAA damage. Thus, the implantation of certain types of living material, like chromaffin cells, can be used as a treatment for disorders caused by a dysfunction in EAA neurotransmission resulting in elevated extracellular EAA levels.

The functionality of the claimed invention will be demonstrated through the use of four examples. In Example 1 it will be demonstrated that adrenal medullary tissue transplants in the spinal subarachnoid space can reduce behavioral symptoms of hyperalgesia and allodynia induced by NMDA receptor activation. This example, however, does not answer the question of how the transplant is able to produce this effect. Furthennore, this example leaves open the question as to whether or not isolated cells could produce the same effect. Therefore, in Example 2, it will be demonstrated that isolated chromaffin cells also have the ability to act as an EAA antagonist. This example will further establish that the rest of the support cells in the adrenal medullary tissue are not needed to obtain the EAA antagonistic effect. Finally, this example will demonstrate that effects seen in Examples 1, 3 and 4 are the result of substances secreted by the chromaffin cells and not the result of the adrenal tissue reinnervating the host tissue. Thus any cell type which secretes EAA antagonists would work sufficiently well. In Example 3, it will be shown that peripheral nerve ligation can have a far reaching effect on the central nervous system. The changes in receptor binding levels are most likely due to either the death of NMDA-receptor containing cells or a generalized down-regulation of the number of NMDA receptors. Either provides strong evidence that there is an increased level of excitatory amino acids present in the spinal cord causing excitotoxic damage. This example will also demonstrate the ability of cell transplants to reverse these pathologic changes. The return of normal levels of NMDA-receptors in the spinal cord provides strong evidence that some type of EAA antagonist is working and thus allowing the host's nervous tissue to normalize NMDA receptor levels. Finally, in Example 4, it will be shown that cellular implants of cells secreting EAA antagonists can reduce motor dysfunction resulting from peripheral nerve damage. Since peripheral nerve damage is thought to lead to spinal cord dysfunction via excessive EAA release, these findings provide further evidence that EAA-initiated neurotoxicity can be reduced and reversed by cellular implants in the CNS.

For the purpose of definition, the term antagonist as used herein is to be interpreted in its broadest sense to include both pharmacological and physiological antagonism. Thus the term antagonist is defined simply as a substance that can interfere, prevent or reverse the action and effect of an agonist.

Unless specifically defined otherwise, all scientific or technical terms used herein have the same meaning as generally understood in the art to which the present invention belongs. All publications mentioned herein are incorporated by reference. Unless mentioned otherwise, the techniques employed herein are standard methodologies well known to one of ordinary skill in the art. Although any similar or equivalent methods and materials can be conveniently adopted in the practice or testing of the invention disclosed herein, the preferred methods and materials are now described.

MATERIALS AND METHODS

EXAMPLE 1

ATTENUATION OF THE EFFECTS OF EXCITATORY AMINO ACID INJECTIONS BY MEDULLARY TISSUE

METHODS
SURGICAL IMPLANTATION

Experimental procedures were approved and carried out in accordance the Guidelines of the Animal Care Committee, University of Illinois at Chicago. Male Sprague-Dawley rats weighing 325–375 g (Sasco, Madison, Wis.) at the beginning of the study were used as both graft donors and recipients. Graft recipients were anesthetized (Nembutal, 40 mg/kg, i.p., supplemented as necessary) and implanted with intrathecal catheters according to methods described by Yaksh and Rudy [T. L. Yaksh and T. A. Rudy, Physiol. Behav., 17:1031–1036 (1976)]. Catheters were made of PE10 tubing with a knot sealed with dental acrylic at 7.5 cm. The catheters were threaded through a slit in the atlanto-occipital membrane to the lumbar spinal subarachnoid space, and the free ends were anchored to the skull using cyanoacrylate. Donor adrenal medullary tissue was dissected from cortical tissue and cut into small pieces (<0.5 cm$^3$). Adrenal medullary tissue from two adrenal glands was used as this amount was shown in previous studies to produce significant antinociception using several behavioral tests [A. T. Hama and J. Sagen, Pain, 52:223–231 (1993); J. Sagen et al., Pain, 42:69–79 (1990); H. Wang and J. Sagen, J. Neural Transplant. Plastic., 5:49–64 (1994)]. Control animals received equal volumes of striated muscle tissue from donors. Graft tissue was implanted in the spinal subarachnoid space via laminectomy at the level of the lumbar enlargement as described previously [J. Sagen et al., Brain Res., 384:189–194 (1986); J. Sagen et al., Pain, 42:69–79 (1990)]. Following surgical procedures, musculature was sutured (4-0 silk), and the skin closed with wound clips. Animals were housed individually and allowed food and water ad libitum.

BEHAVIORAL ASSESSMENT

Animals were allowed to recover from surgical procedures for two weeks prior to commencement of behavioral testing. Responses to noxious and innocuous stimuli were determined using three tests sequentially: the Hargreaves model for thermal hyperalgesia [K. M. Hargreaves et al., Pain, 32:223–231 (1988)], the Randall-Selitto test for mechanical hyperalgesia, and von Frey thresholds for tactile allodynia. To assess response to a noxious thermal stimulus, rats were placed on an elevated glass floor beneath an inverted clear plastic cage, and a radiant heat source beneath the glass was aimed at the plantar surface of the hindpaw. The onset of light activated a timer which was terminated by a hindpaw withdrawal response. A cutoff time of 15 sec was used to avoid tissue damage in the absence of a response. Testing was alternated between both hind paws for 3 trials 30 sec apart, the average values defined as the paw withdrawal latency for statistical analyses. The Randall-Selitto test was elicited by a commercially available apparatus (Ugo-Basile) that applies pressure at a constant rate of 64 g/sec. The force was applied to the ventral surface of both hindpaws sequentially until the animal reacted with a withdrawal response (average of both sides). The apparatus automatically terminates at a scale reading of 25 (=1000 g). For assessment of tactile allodynia, a series of calibrated von Frey hairs, ranging from 3.6–75.9 g were used. Animals were placed on an elevated wire mesh surface an von Frey hairs were indented on the hind paw mid-plantar skin until they just bent 5 times at a frequency of approximately 2/sec [Z. Seltzer et al., Pain, 43:205–218 (1990)]. Testing was alternated between both hind paws until withdrawal threshold was reached (average of both sides). The series of behavioral tests took approximately 5–6 min to complete.

EXPERIMENTAL PROTOCOL

The first group of animals was used in order to determine the time course and dose-responsiveness to intrathecally injected NMDA. NMDA (Sigma Chemical Co., St. Louis, Mo.) was dissolved in saline (pH 7.2–7.4) just prior to use on each test day. Baseline responses to all three tests were assessed at the beginning of each test day prior to drug injection. Following baseline determinations, animals with either adrenal medullary (n=10) or control (n=10) transplants received intrathecal injections of NMDA (1.0, 5.0, 10.0, or 50.0 nmol) or saline vehicle in 15 μl volumes, followed by 10 μl saline flush. The intermediate doses were chosen based on previous reports of thermal hyperalgesia in this dose range [A. B. Malmberg and T. L. Yaksh, Science, 257:1276–1279 (1992); A. B. Malmberg and T. L. Yaksh, Pain, 54:291–300 (1993)]. Although other laboratories have reported hyperalgesic effects at lower doses of NMDA, pilot injections in our laboratory indicated that doses lower than 1.0 nmol were ineffective using our behavioral assessments. The high dose was used in order to determine the ability of adrenal medullary transplants to attenuate behavioral allodynia and hyperalgesia when exposed to high levels of NMDA. Responses to behavioral stimuli were again assessed at 5, 15, 30, 45, and 60 min following NMDA administration. Due to behavioral agitation during the first 5 min following administration of the high dose (50 nmol), behavioral testing commenced with the 15 min assessment following this dose. Animals were tested at weekly intervals and doses of NMDA were administered in random order, such that all animals eventually received each NMDA dose.

In a second group of animals, the effect of pretreatment with either opiate antagonist naloxone (HCl, 2.0 mg/kg, s.c., Sigma Chemical Co., St. Louis, Mo.), α-adreneryic antagonist phentolamine (mesylate, 10.0 mg/kg, s.c., Sigma Chemical Co., St. Louis, Mo.), or saline vehicle on NMDA-induced hyperalgesia and allodynia was determined, in order to assess the possible role of opioid peptides and catecholamines in mediating the behavioral effects of adrenal medullary transplants. These antagonist doses were chosen since they were found to block antinociceptive effects of adrenal medullary transplants in acute analgesiometric tests. Intennediate doses of NMDA (2.5, 5.0, and 10.0 nmol) were used, as behavioral responses between adrenal medullary and control implanted groups in this range were clearly distinguishable, and thus a reversal to control response latencies or thresholds would be apparent. Animals with either adrenal medullary or control transplants were pretreated with antagonist or vehicle 20 min prior to intrathecal NMDA injection. Behavioral responses were again assessed 30 min following NMDA injection, as this was determined in the previous group to be the time of peak drug effect. Animals were tested at weekly intervals with antagonists and vehicle given in random order (n=10 animals per drug-dose combination).

MORPHOLOGICAL AND STATISTICAL ANALYSIS

Statistical comparisons between treatment groups was done using ANOVA for repeated measures and the Newman-Keuls test for multiple post-hoc comparisons (SigmaStat, Jandel Scientific). To estimate relative NMDA potencies between groups, dose-response curves and potency ratios were calculated.

RESULTS

Figure 2:
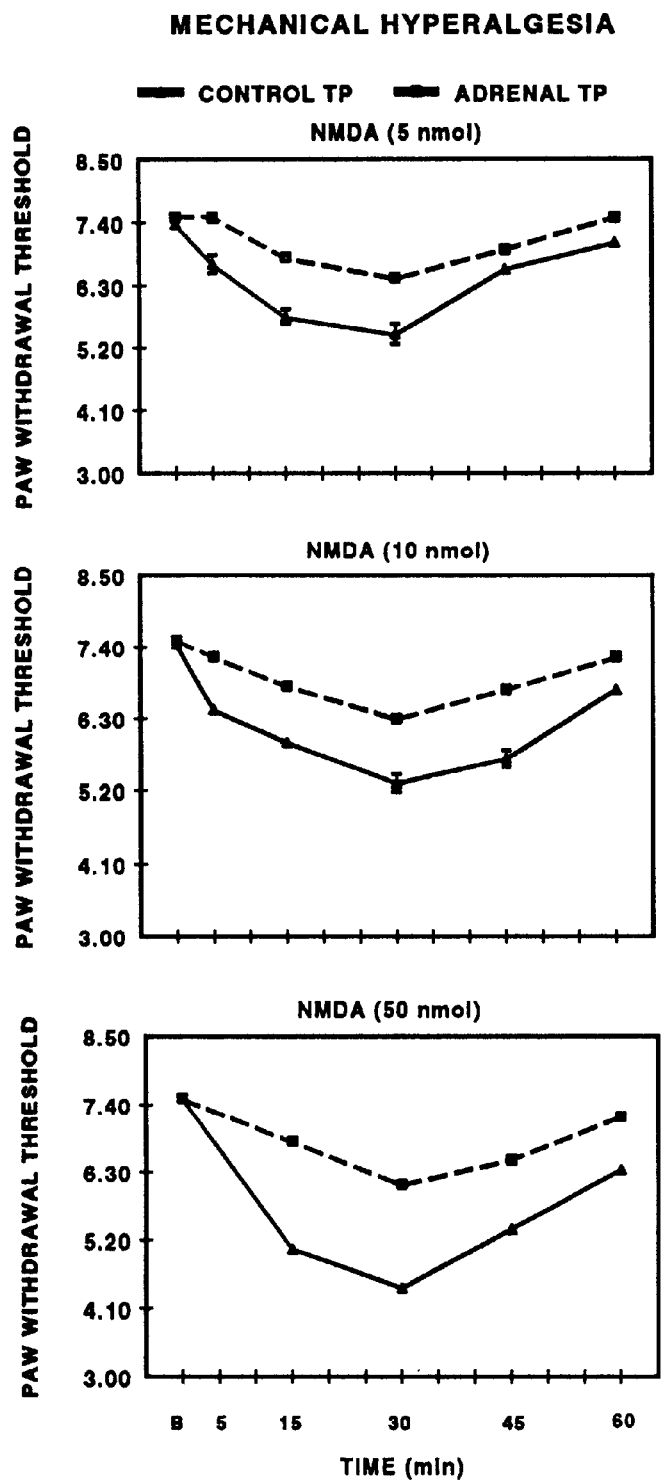
FIG. 2: Time course of mechanical hyperalgesia induced by 5 nmol (top panel), 10 nmol (middle panel) and 50 nmol (lower panel) NMDA injected intrathecally in rats with adrenal medullary (squares) and control striated muscle (triangles) transplants in the spinal subarachnoid space. The ordinate is the paw withdrawal threshold (scale reading) to increasing mechanical pressure. The abscissa is time (min) alter intrathecal NMDA injection. B (baseline) indicates withdrawal latencies prior to NMDA injection. All data is presented as mean+/− S.E.M., although several standard errors bars were small and thus masked by the computer generated symbols. N=10 animals per group.
Figure 3:
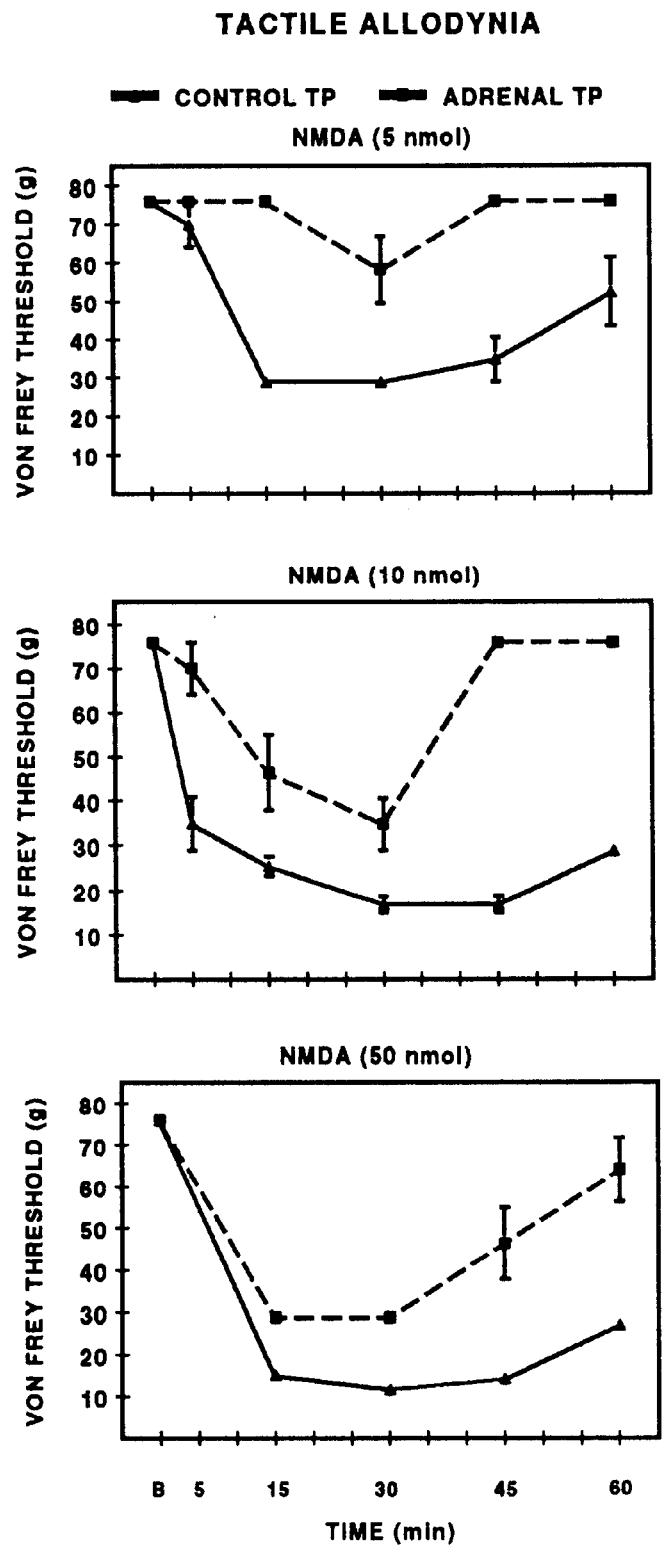
FIG. 3: Time course of tactile allodynia induced by 5 nmol (top panel), 10 mnol (middle panel) and 50 nmol (lower panel) NMDA injected intrathecally in rats with adrenal inedullary (squares) and control striated muscle (triangles) transplants in the spinal subarachnoid space. The ordinate is the withdrawal threshold to a calibrated series of von Frey hairs of increasing weights. The abscissa is time (min) after intrathecal NMDA injection. B (baseline) indicates withdrawal latencies prior to NMDA injection. All data is presented as mean +/− S.E.M., although several standard errors bars were small and thus masked by the computer generated symbols. N=10 animals per group.

The time course of behavioral responses to intrathecally injected NMDA in adrenal medullary and control transplanted animals is shown in FIGS. 1–3. Prior to NMDA injection, baseline responses between transplant groups were not different. In addition, administration of NMDA on previous testing days did not alter baseline behavioral responses, suggesting full recovery from NMDA-induced hyperalgesia and allodynia after acute administration. FIG. 1 shows the response to a noxious thermal stimulus following intrathecal injection of 5.0 (top panel), 10.0 (middle panel), or 50.0 (bottom panel) nmol NMDA. The response to 1.0 nmol NMDA is not shown since it was not significantly different than saline injections in either transplant group (P>0.05). At all three NMDA doses shown, thermal hyperalgesia was significantly attenuated compared to control transplanted animals (overall F (df 1,5)=1583.9, 1644.2, and 1640.2, P<0.01, for 5.0, 10.0, and 50.0 nmol, respectively). The attenuation in hyperalgesia in adrenal medullary implanted animals was apparent in terms of onset, peak severity, and duration. For example, the 5 nmol NMDA dose produced significant hyperalgesia (P<0.05) within 5 min post-injection in control animals, while withdrawal latencies in adrenal medullary implanted animals were not reduced until 30 min post-injection. In addition, withdrawal latencies were recovered to pre-injection baseline by 45 min after 5 nmol NMDA injection in adrenal medullary implanted animals (P>0.05), while hyperalgesia was still observed in control transplanted animals 60 min post-injection (P<0.05). The protective effects of adrenal medullary transplants were apparent even at extremely high doses of NMDA (50 nmol), although significant thermal hyperalgesia was induced in these animals (P<0.05). In all cases, the peak effect of intrathecally administered NMDA was 30 min post-injection, with a tendency towards pre-injection latencies at later times.

FIG. 2 shows the response to a noxious mechanical stimulus following intrathecal injection of 5.0 (top), 10.0 (middle), and 50.0 (bottom) nmol NMDA. Similar to thermal nociceptive responses, NMDA produced mechanical hyperalgesia with peak effect at 30 min post-injection. Adrenal medullary transplants significantly attenuated this response at all three NMDA doses (overall F (df 1,5)=96.7, 145.2, and 539.3, P<0.01, for 5.0, 10.0, and 50.0 nmol, respectively). FIG. 3 reveals similar effects on responses to innocuous tactile stimuli. Tactile allodynia was significantly attenuated in adrenal medullary compared to control implanted animals (overall F (df 1,5)=57.8, 172.1, and 106.3, P<0.01, for 5.0, 10.0, and 50.0 nmol, respectively). In contrast to thermal and mechanical hyperalgesia, recovery towards pre-injection baseline responses to innocuous tactile stimuli appeared prolonged in control transplanted animals, particularly at higher doses of NMDA. This recovery period was reduced in adrenal medullary transplanted animals.

Figure 4:
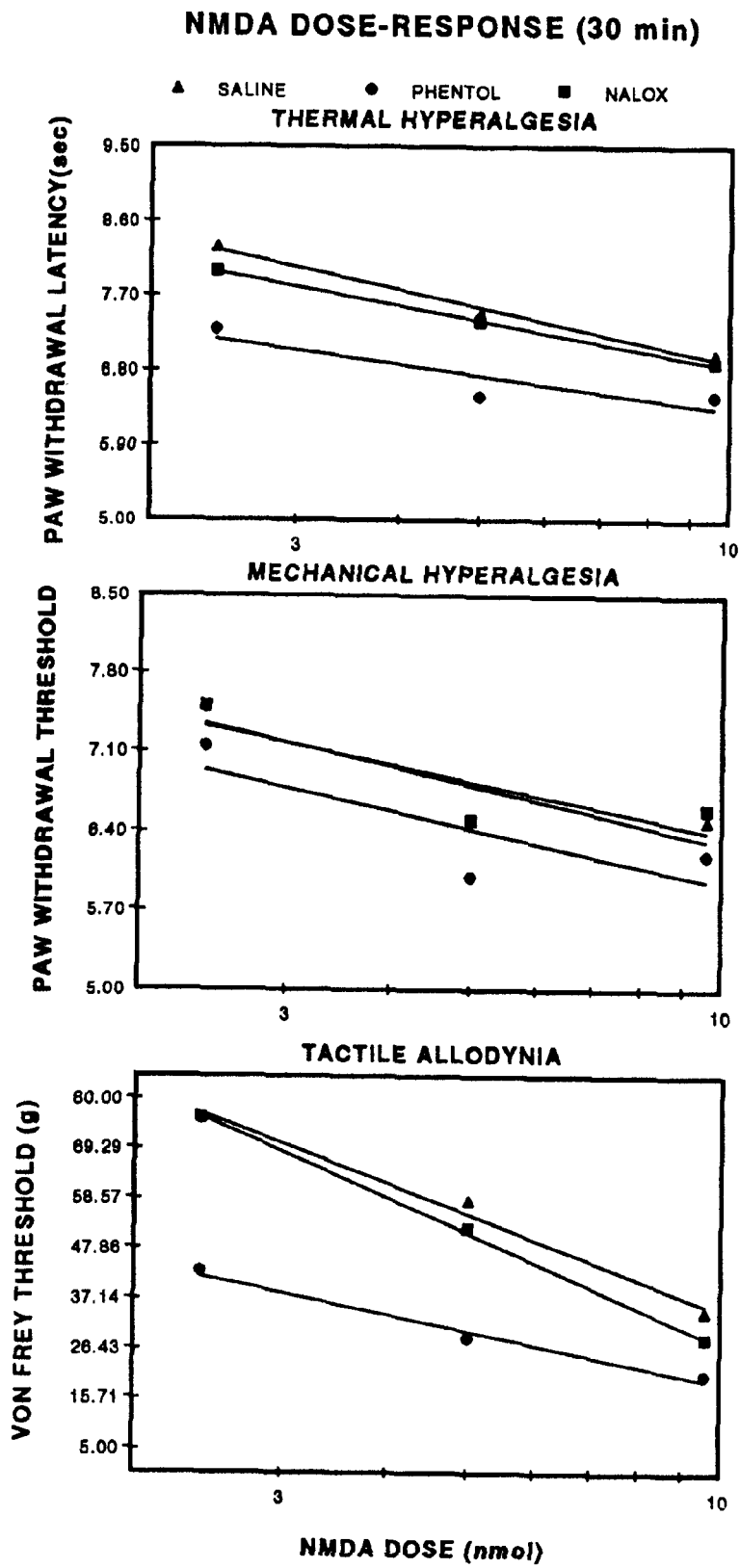
FIG. 4: Computer-generated dose-response curves to intrathecal NMDA at the time of peak responsiveness (30 min post-injection). Responses to noxious thennal (top panel), noxious mechanical (middle panel) and innocuous tactile (lower panel) stimuli in animals with adrenal medullary (squares, n=10) or control (triangles, n=10) transplants in the spinal subarachnoid space. The ordinate is latency or threshold for response to stimuli (mean+/−S.E.M.). The abscissa is NMDA dose plotted on a log scale.

FIG. 4 shows summary dose-response curves for intrathecal NMDA in animals with adrenal medullary and control transplants at the time of peak drug effect (30 min). Over the dose range of 1.0–50.0 nmol, dose-response curves are significantly shifted upward as assessed by responses to noxious thermal (upper panel), noxious mechanical (middle panel), and innocuous tactile (lower panel) stimuli in adrenal medullary transplanted animals (F (df 1,3)=1388.8, 509.5, and 42.7, respectively, P<0.01). Estimated potency ratios were 6.0, 7.1, and 3.1 for control compared to adrenal transplanted animals as assessed by the three tests. Although adrenal medullary transplants reduced exaggerated responses to all three stimuli, these results illustrate more potent effects on noxious stimuli.

Figure 5:
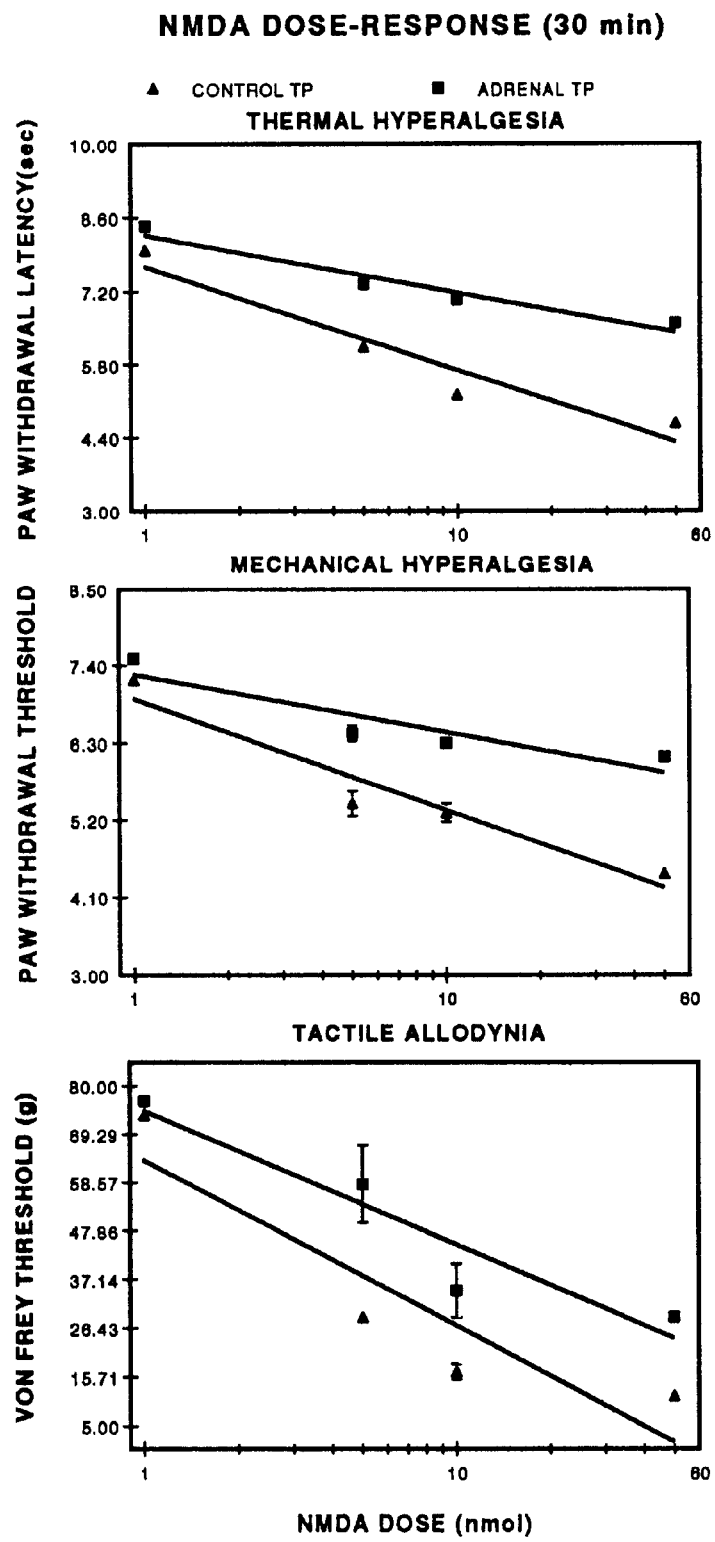
FIG. 5: Computer-generated dose-response curves to intrathecal NMDA in animals with adrenal medullary transplants following pretreatment with either saline vehicle (triangles), α-adrenergic antagonist phentolamine (circles, 10.0 mg/kg, s.c.) or opiate antagonist naloxone (squares, 2.0 mg/kg, s.c.) 20 min prior to NMDA injection (n=10 animals per treatment). The ordinate is latency or threshold for response to stimuli (mean+/−S.E.M.). The abscissa is NMDA dose plotted on a log scale.
Figure 6:
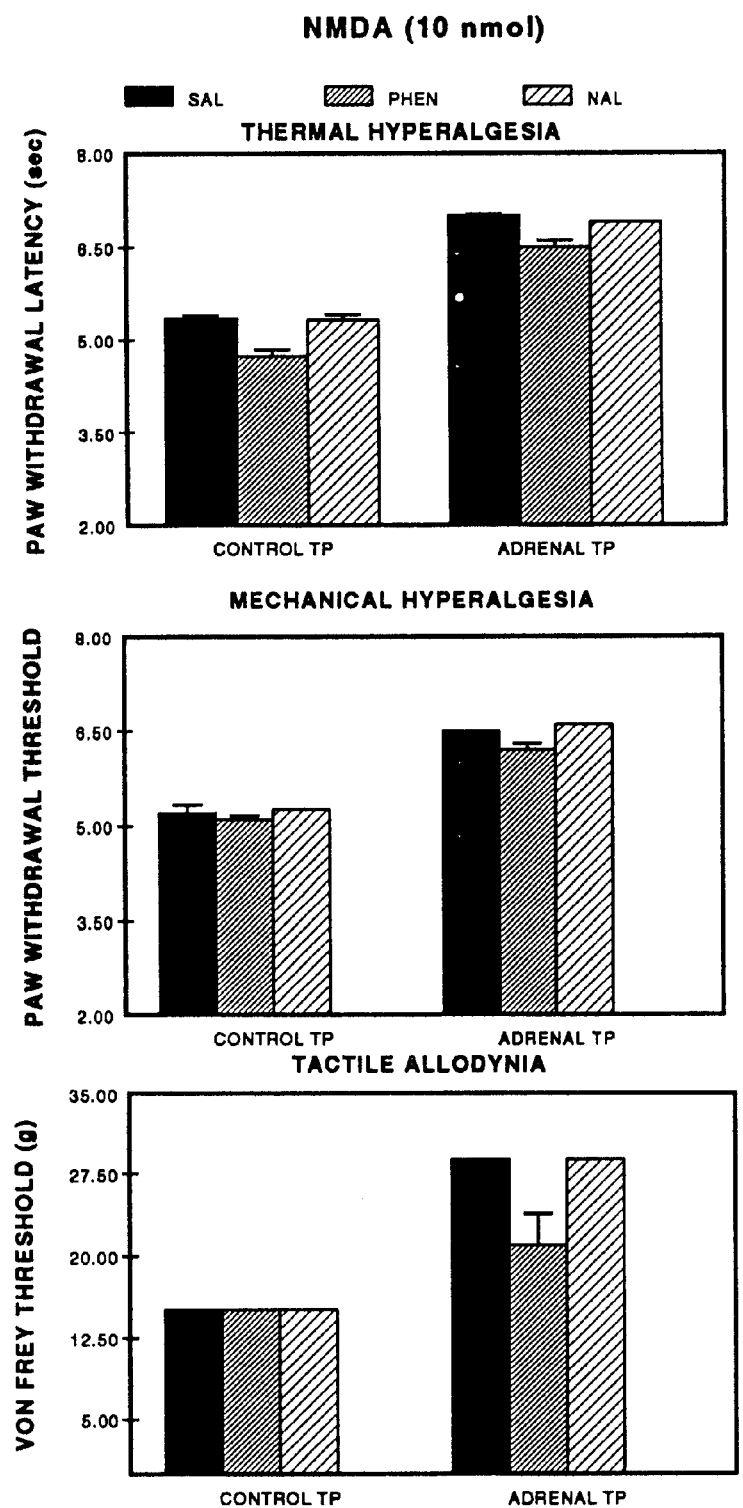
FIG. 6: Effect of pretreatment with saline vehicle (solid bars), α-adrenergic antagonist phentolamine (narrow cross-hatches), or opiate antagonist naloxone (wide cross-hatches) on responses to noxious thermal (top panel), noxious mechanical (middle panel), and innocuous tactile (lower panel) stimuli 30 min following intrathecal injection of NMDA (10 nmol). The left aroup of bars on each graph are responses (mean+/−S.E.M.) in control transplanted animals (n=10); the right group are responses in adrenal medullary transplanted animals (n=10).

In order to assess the possible contribution of either opioid peptides or catecholamines released from transplanted adrenal inedullary cells in the attenuation of NMDA-induced hyperalgesia and allodynia, responses to intermediate doses of NMDA were determined following pretreatment with antagonists. Pretreatment with naloxone had no effect on the NMDA dose-response curves for noxious thennal stimuli (FIG. 5, top panel), noxious mechanical stimuli (FIG. 5, middle panel), or innocuous tactile stimuli (FIG. 5, bottom panel) compared to saline pretreatment (P>0.05) in adrenal medullary transplanted animals. In contrast, phentolamine pretreatment significantly shifted the dose-response curves downward (P<0.01 for thermal hyperalgesia and tactile allodynia; P<0.05 for mechanical hyperalgesia) compared to saline pretreatment. Thus, phentolamine pretreatment reduced the potency of adrenal medullary transplants in alleviating NMDA-mediated hyperalgesia and allodynia. However, this pretreatment dose did not completely eliminate the beneficial effects of the transplants, as the responses were not reduced to levels in control transplanted animals. As illustrated in FIG. 6, some residual NMDA blocking effects are still observed in adrenal medullary compared to control transplanted animals as assessed by all three tests (P<0.05), even following phentolamine pretreatment.

Thus the results of this example demonstrate that adrenal medullary tissue transplants in the spinal subarachnoid space can reduce behavioral symptoms of hyperalgesia and allodynia induced by NMDA receptor activation.

EXAMPLE 2

ATTENUATION OF THE EFFECTS OF EXCITATORY AMINO ACID INJECTIONS BY SECRETORY PRODUCTS FROM HIGH-$K^+$ STIMULATED CHROMAFFIN CELLS

METHODS

ISOLATION OF BOVINE CHROMAFFIN CELLS (BCC)

Bovine chromaffin cells were isolated as described by Ortega et al. [J. D. Ortega and J. Sagen, Exp. Brain Res., 95:381 (1993)]. Bovine adrenal glands were purchased from a local abbatoir, trimmed of their fat, and immediately perfused with $Ca^{2+}$ and $Mg^{2+}$-free Locke's solution [1.5 M NaCl, 0.05 M KCl, 0.04 M $NaHCO_3$, 0.06 M glucose, 0.05 M N-2-hydroxyethylpiperazine-N'-2-ethanesulfonic acid (HEPES) at pH 7.2, 37° C.] containing antibiotics [penicillin/steptomycin (100 U/ml), kanamycin (25 µg/ml)] and antifungal agents [Fungizone] (amphotericin B, 0.125 µg/ml]. Following a 30-min incubation in Locke's solution, the glands were perfused with a 0.1% collagenase solution [Boehringer Mannheim]: 0.05% (w/v) bovine serum albumin (BSA; Simga) and 0.01% (w/v) trypsin inhibitor (Sigma)] for 30 min. After this perfusion, the inedullary tissue was dissected from the surrounding cortex, minced and filtered through a fine nylon mesh, and washed several times with Locke's solution before purifying the cell population with a Percoll gradient. The washed cells were placed on a self-generating, buoyant density gradient (45 ml of Percoll, 5ml of 10X Locke's solution at pH 7.4) and spun at 12,000 rpm for 20 min in a refrigerated centrifuge (IEC B20, Needhamitts, 4° C.). The band containing healthy chromaffin cells, as defined by morphological analysis, was removed from the gradient, washed several times with Locke's solution, and plated on 100 mm tissue culture dishes in medium [Dulbecco's modified Eagle's medium (DMEM) and Ham's F-12 (1:1 DMEM:F12)] supplemented with 5% (v/v) fetal bovine serum (FBS), antibiotics (penicillin/streptomycin, 100 U/ml; gentamicin, 50 µg/ml), and antifungal agents (Fungizone, 0.125 µg/ml). The plates were placed in an incubator overnight (37° C., 5% $CO_2$) to allow for differential adherence of unwanted cell types such as fibroblasts and endothelial cells. The next day chromaffin cells were removed from their plates by gentle agitation, and once again placed on a Percoll gradient to further enhance the purity and viability of the final chromaffin cell population. Trypan blue exclusion generally places the viability of all chromaffin cell preparations in excess of 95%. Approximately $5\times10^6$ cell were plated on each plate.

RELEASE OF SECRETORY PRODUCTS FROM CHROMAFFIN CELLS

The media was removed from the cells and was replaced with 5 ml Hank's Balanced Salt Solution (HBSS) containing high K$^+$ (60 mM KCl) to stimulate the release of secretory products from the chromaffin cells. The chromaffin cells were allowed to remain in the high K$^+$ HBBS for 15 minutes. After the 15 minutes, the cells were removed from the high K$^+$ HBBS, frozen and lyophilized. To remove salts, the preperation was reconstituted in 0.2 N HCl and extracted on Sep-Pak cartridges (Waters, Milford, Mass.). Eluate was collected from the columns with 60% acetonitrile in a 0.1% trifluoroacetic acid, and lyopilized. The result was then reconstituted in 500 µl of water as a preparation for injection. As a control (vehicle) 5 ml of fresh high K$^+$ HBBS was also desalted and lyophilized using identical procedures, then reconstituted in 500 µl of water as a preparation for injection.

EXPERIMENTAL PROTOCOL

Graft recipients were anesthetized (Nembutal, 40 mg/kg, i.p., supplemented as necessary) and implanted with intrathecal catheters according to methods described by Yaksh and Rudy [T. L. Yaksh and T. A. Rudy, Physiol. Behav., 17:1031–1036 (1976)]. Catheters were made of PE10 tubing with a knot sealed with dental acrylic at 7.5 cm. The catheters were threaded through a slit in the atlanto-occipital membrane to the lumbar spinal subarachnoid space, and the free ends were anchored to the skull using cyanoacrylate.

To test the effects of the secretory products of chromaffin cells against EAA agonists, the Hargreaves model for thermal hyperalgesia was chosen (details of this test are described above). NMDA (Sigma Chemical Co., St. Louis, Mo.) was dissolved in saline (pH 7.2–7.4) just prior to use on each test day. Baseline responses were assessed in all rats. Following baseline determinations, half the animals were given a 15 µl intrathecal injection of reconstituted chromaffin cell secretory products (secretory products from approx. 150,000 cells) and the other half a 15 µl intrathecal injection of the reconstituted control (vehicle). Both injections were followed by a 10 µl saline flush. After 10 mninutes, all animals were given an intrathecal injection of NMDA (100 nmol). Following an additional 15 minute wait, all animals were retested. The next day, the experiment was repeated, with the animals receiving injections of secretory products now receiving control injections and visa versa.

RESULTS

Figure 7:
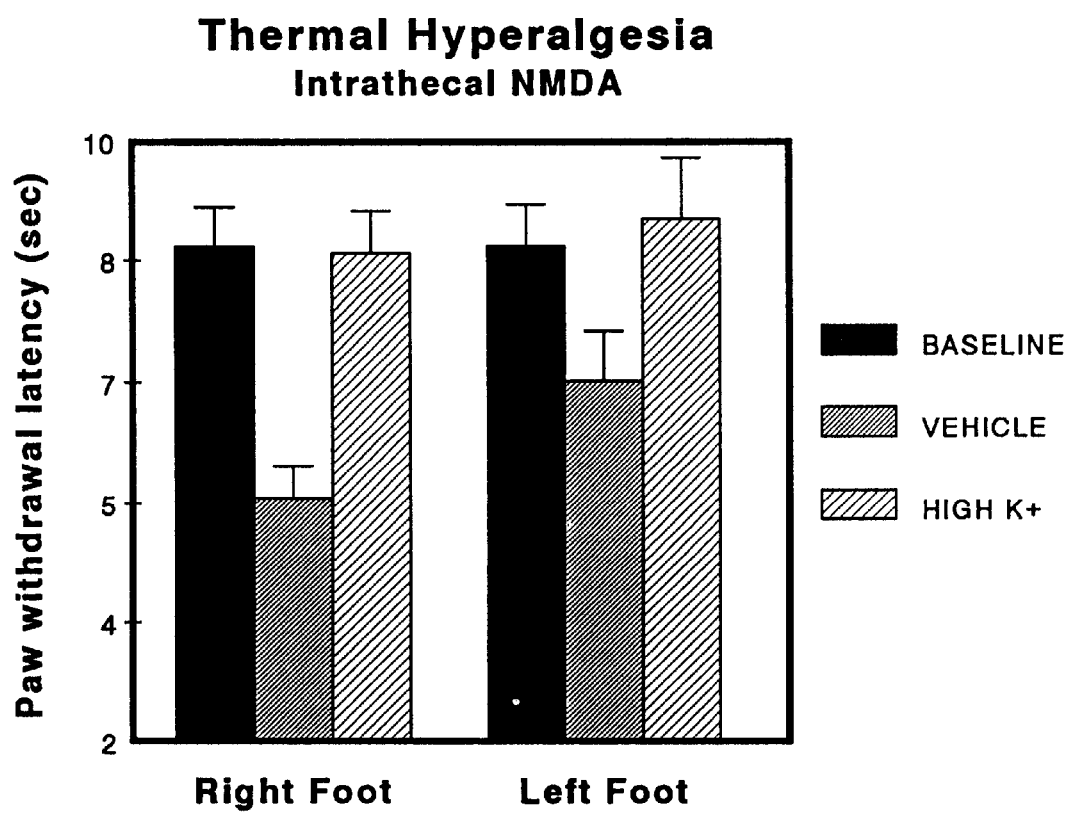
FIG. 7: Effect of pretreatment with secretory products released from isolated bovine chromaffin cells (narrow cross-hatches) and control vehicle (wide cross-hatches) compared to baseline responses (solid bars) to noxious thermal stimuli 15 minutes after injection of NMDA (100 nmol). The ordinate is latency to stimuli (mean+/−S.E.M.).

In order to make sure that the effects seen in example 1 were the result of products actually secreted by chromaffin cells, the effects of just chromaffin secretory products were assessed. As shown in FIG. 7, the pretreatment of animals with substances released from isolated chromaffin cells significantly reduced the responses to noxious thermal stimuli following i.t. injections of NMDA when compared to the baseline. Furthermore, this reduction in response was only seen by pretreating the animals with the secretory products of isolated chromaffin cells and not from the vehicle used to perform the injections. This example establishes that isolated chromaffin cells also have the ability to act as an EAA antagonist. It further establishes that the rest of the support cells in the adrenal medullary tissue are not needed to obtain this EAA antagonistic effect. Finally, this example demonstrates that effects seen in examples 1, 3 and 4 are the result of substances secreted by the chromaffin cells and not the result of the adrenal tissue reinnervating the host tissue. Thus any cell type which secretes EAA antagonists would work sufficiently well.

EXAMPLE 3

CHANGES IN NMDA RECEPTOR EXPRESSION FOLLOWING NERVE INJURY

METHODS

The distribution of spinal NMDA receptors is controversial, most likely due to the diversity in subunit composition and ligand binding sites. Thus, in the current example, both receptor binding sites using a high affinity radioligand for the glutamate binding site of the NMDA receptor and NMDAR1 distribution using immunohistochemistry were used as complementary approaches. Unless otherwise stated, all reagents were of analytical grade and obtained from Sigma (St. Louis, Mo.).

ANIMALS AND SURGICAL PREPARATION

Male Sprague-Dawley rats (200–250 g; purchased from Sasco, WI) were used as both graft donors and recipients. Peripheral nerve injuries were induced using the chronic constriction injury model [G. J. Bennett and Y. K. Xie, Pain, 33:87–107 (1988)], which produces a characteristic spectrum of exaggerated sensory responsiveness to noxious and innocuous stimuli similar to that found clinically in peripheral nerve-injured patients. Animals were anesthetized (sodium pentobarbital, 40 mg/kg, i.p.), and the right common sciatic nerve was exposed under aseptic conditions. The sciatic nerve was ligated with four 4-0 chromic gut ligatures, as previously described [G. J. Bennett and Y. K. Xie, Pain, 33:87–107 (1988); A. T. Hama and J. Sagen, Pain, 52:233–231 (1993); A. T. Hama and J. Sagen, Brain Res., 640:345–351 (1994); A. T. Hama and J. Sagen, Brain Res., 651:183–193 (1994)]. No surgery was done on the left side for comparison in ligand binding studies. Following nerve ligation, the musculature was sutured with 3-0 silk and the skin closed with wound clips.

Two weeks following unilateral nerve ligation, animals received adrenal medullary transplants in the spinal subarachnoid space as described previously [A. T. Hama and J. Sagen, Pain, 52:233–231 (1993); A. T. Hama and J. Sagen, Brain Res., 640:345–351 (1994); J. Sagen et al., Pain, 42:69–79 (1990)]. Adrenal medullary tissue was dissected from the adrenal glands of donor rats, and cut into small pieces (<0.5 mm$^3$) for implantation. Adrenal medullary tissue from 2 glands was used, as this has been shown to produce significant and reproducible antinociception in previous studies [H. Wang and J. Sagen, J. Neural Transpl. Plast., 5:49–64 (1994)]. Transplant control animals received equal volumes of striated muscle tissue from donor animals. For implantation, a laminectomy was perfonned to expose lumbar segments L1–L2, and tissue was implanted in the subarachnoid space via a slit in the dura and arachnoid membranes. Following implantation, the back musculature was sutured with silk and the skin closed with wound clips. Age-matched rats were used as unoperated controls.

In order to confirm the severity of peripheral nerve injury and the efectiveness of adrenal medullary transplants in alleviating hyperalgesia, animals were assessed for responsiveness to a noxious heat stimulus [K. M. Hargreaves et al., Pain, 32:223–231 (1988)]. As described in previous studies in our laboratory, animals with constriction injury displayed significant thermal hyperalgesia on the ligated side at 1 and 2 weeks following nerve injury, and this was reversed by adrenal medullary, but not control transplants [A. T. Hama et J. Sagen, Pain, 52:223–231 (1994); A. T. Hama and J. Sagen, Brain Res., 640:345–351 (1994)].

RECEPTOR-LIGAND BINDING ASSAY

Changes in NMDA receptor levels were determined at three weeks following nerve injury (one week following transplantation), as a marked distinction in responses to sensory stimuli between adrenal medullary and control transplanted animals can be made at this time point. Further, at this stage following peripheral nerve injury, robust induction of spinal NADPH-d is apparent, also reduced by adrenal medullary transplants [A. T. Hama and J. Sagen, Brain Res., 640:345–351 (1994)]. [$^3$H]CGP-39653 (D,L-(E)-2-amino-4-propyl-5-phosphono-3-pentenoate), a selective high-affinity competitive antagonist at NMDA receptors, was used to label the binding sites. In preliminary experiments, binding characteristics of this ligand were determined in the rat spinal cord. Saturation assays were performed on whole spinal cord tissue, and the results compared to those obtained in cortical membranes. NMDA binding sites were analyzed using previously described procedures with slight modification [M. A. Sills et al., Eur. J. Pharmacol., 192:19–24 (1991)]. Animals were decapitated and the spinal cords were rapidly extruded with saline pressure. For comparison, neocortex was dissected. Tissue was homogenized in 50 volumes of 5.0 mM Tris-HCl (pH=7.7 at 25° C.) and centrifuged at 48,000×g. The supernatant was discarded and the pellet resuspended in 20 volumes of 10 mM EDTA in 5 mM Tris-HCl. The suspension was incubated for 10 min. at 37° C. in a shaking water bath. After centrifugation, the membrane preparation was washed twice by resuspending in Tris-HCl and centrifuging as before. The pellet was resuspended in Tris-HCl and frozen for at least 4 days at -20° C. before assay. On the day of assay, the membranes were slowly thawed and washed twice in Tris-HCl. The final pellet was resuspended in 12.5 volumes (original wet weight) of Tris-HCl. Assay tubes containing [$^3$H]CGP-39653 (35.2 Ci/mmol, NEN-Dupont, Boston, Mass.) and 100 µl of tissue in a final volume of 1.0 ml were run in triplicate. This volume of tissue corresponded to approximately 110 µg of protein as determined using the Bradford method (BioRad, Richmond, Calif.). Saturation curves were generated using eight different concentrations of radioligand ranging from 0.4 to 60.0 nM. Nonspecific binding was determined in parallel tubes containing 100 mM L-glutamiate. After incubation for 1 hr at 4° C., tissues were filtered using a Brandel tissue harvester over S&S #32 glass fiber filters, and washed three times with ice-cold Tris-HCl. Radioactivity was counted with a Beckman 3270 scintillation counter at 48–52% efficiency. Estimates of binding parameters were determined using the program LIGAND [P. J. Munson and D. Rodbard, Anal. Biochem., 197:220–239 (1980)].

For determination of changes in binding in nerve-injured animals, lumbar segments $L_4$–$L_5$, the level of sciatic nerve distribution, were dissected and split into left (contralateral to nerve ligation) and right (ipsilateral) halves. Contralateral and ipsilateral segments were each pooled from three animals in order to reliably measure binding site concentrations. Five pooled groups in each treatment paradigm (nerve-injured animals with adrenal transplants, nerve-injured animals with control transplants, and intact non-ligated animals) were compared. Binding assays were performed as described above using 10 nM [$^3$H]CGP-39653. Differences in NMDA binding in treatment groups were statistically analyzed using ANOVA and the Newman-Keuls test for multiple post-hoc comparisons.

IMMUNOCYTOCHEMISTRY

The distribution of spinal NMDA receptors after peripheral nerve injury and transplantation was also analyzed imrnunocytocherically as a complementary approach, as discrepancies in NMDA receptor subunit and ligand binding distribution have been noted [T. Furuyama et al., Mol. Brain Res., 18:141–150 (1993); R. S. Petalia et al., J. Neurosci, 14:667–696 (1994)]. In vitro studies indicate that heteromeric NMDA receptors composed of the NMDAR1 with NR2 subunits show high-affinity NMDA binding [T. Kutsuwada et al., Nature, 358:36–41 (1992)]. However, homomeric NMDA receptors composed of NMDAR1 subunits are functional as well, indicating the importance of the NMDAR1 subunit in receptor function. A separate set of animals (n=3 from each treatment group) were deeply anesthetized (sodium pentobarbital, 50 mg/kg, i.p.), transcardially cleared with saline and perfused with 4% phosphate-buffered paraformaldehyde. Lumbar regions $L_4$–$L_5$ were dissected and cryoprotected in 20% sucrose for 48 hrs at 4° C. Frozen sections (25 µm) were cut on a cryostat and collected in phosphate-buffered saline (PBS; pH=7.4). Sections were blocked in 2% normal goat serum in PBS for 30 min., then incubated in NMDAR1 subunit polyclonal antibody (1:100; Chemicon, Temecula, Calif.) for 24 hrs. at 4° C. Sections were washed in PBS, incubated with a biotin-conjugated secondary antibody (Vectastain ABC kit; Vector Laboratories, Burlingame, Calif.) and reacted in a solution of tris-buffered saline (pH=7.4) containing 0.025% diaminobenzidine, 0.01% $H_2O_2$ and 0.67% nickel ammonium sulfate. Adrenal medullary graft viability was confirmed using tyrosine hydroxylase (Incstar, Stillwater, Minn.) immunocytochemistry as described in previous studies [A. T. Hama and J. Sagen, Pain, 52:233–231 (1993); A. T. Hama and J. Sagen, Brain Res., 640:345–351 (1994); J. Sagen et al., Pain, 42:69–79 (1990)].

RESULTS

RECEPTOR-LIGAND BINDING

Figure 8:
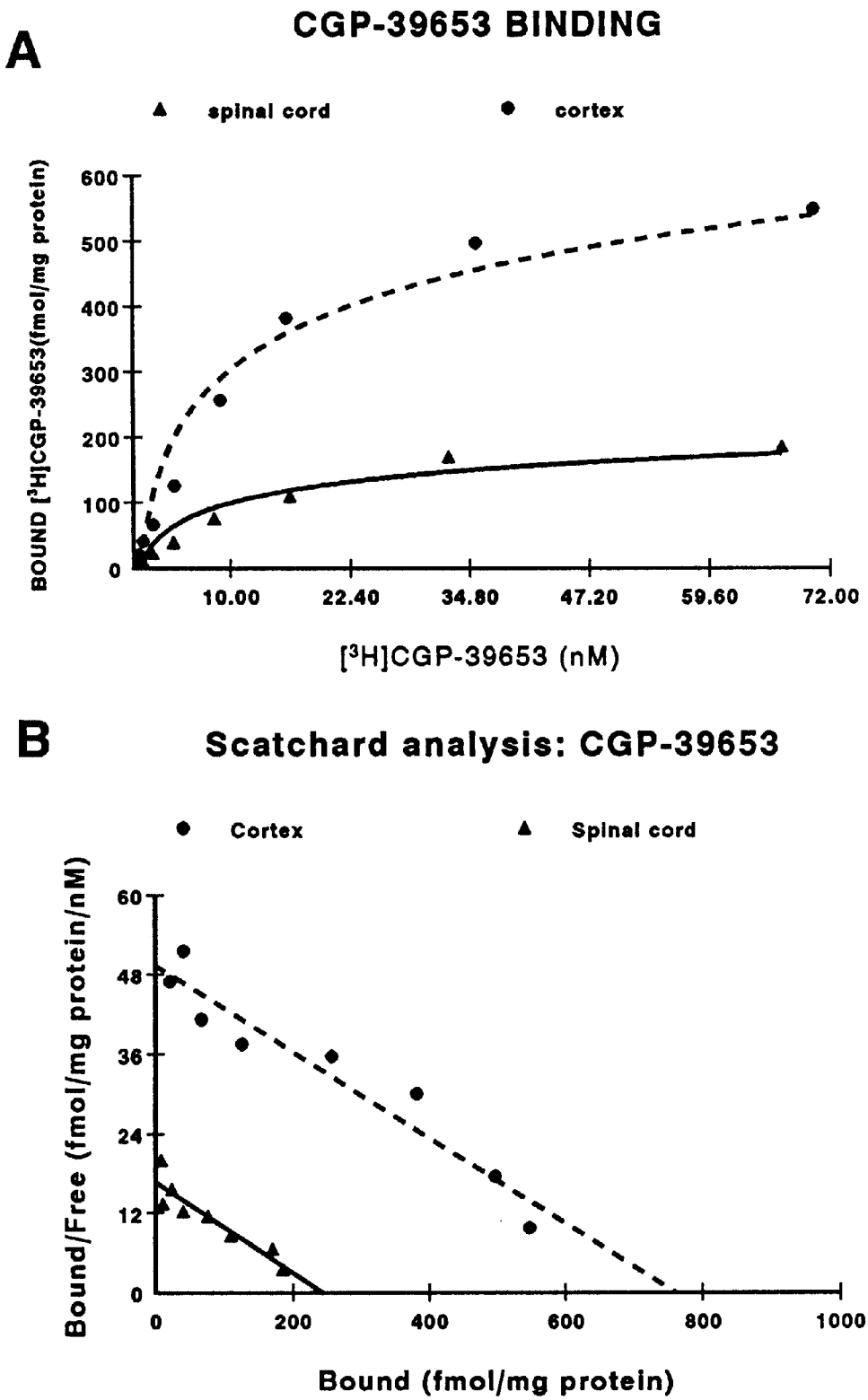
FIG. 8: Saturation curves (A) and Scatchard analysis (B) of [$^3$H]CGP-39653 binding in normal, unoperated rat cortical and spinal tissues. Scatchard analysis demonstrated one-site binding, with $K_D$ 15.4 nM and $B_{max}$ 760.0 fmol/mg protein in cortex and $K_D$ 12.9+/−1.8 and $B_{max}$ 224.9 +/−18.8 fmol/mg in spinal cord.

Binding studies in spinal cords and cortices of normal intact animals revealed that [$^3$H]CGP-39653 labels one binding site in a saturable manner in both regions (FIG. 8). The binding affinity in the spinal cord was similar to cerebral cortex ($K_D$spinal cord=12.9+/-1.8 nM vs $K_D$cortex=15.4 nM). However, the number of binding sites was lower ($B_{max}$spinal cord=224.9+/-18.8 fmol/mg protein vs $B_{max}$cortex=760 fmol/mg protein).

Figure 9:
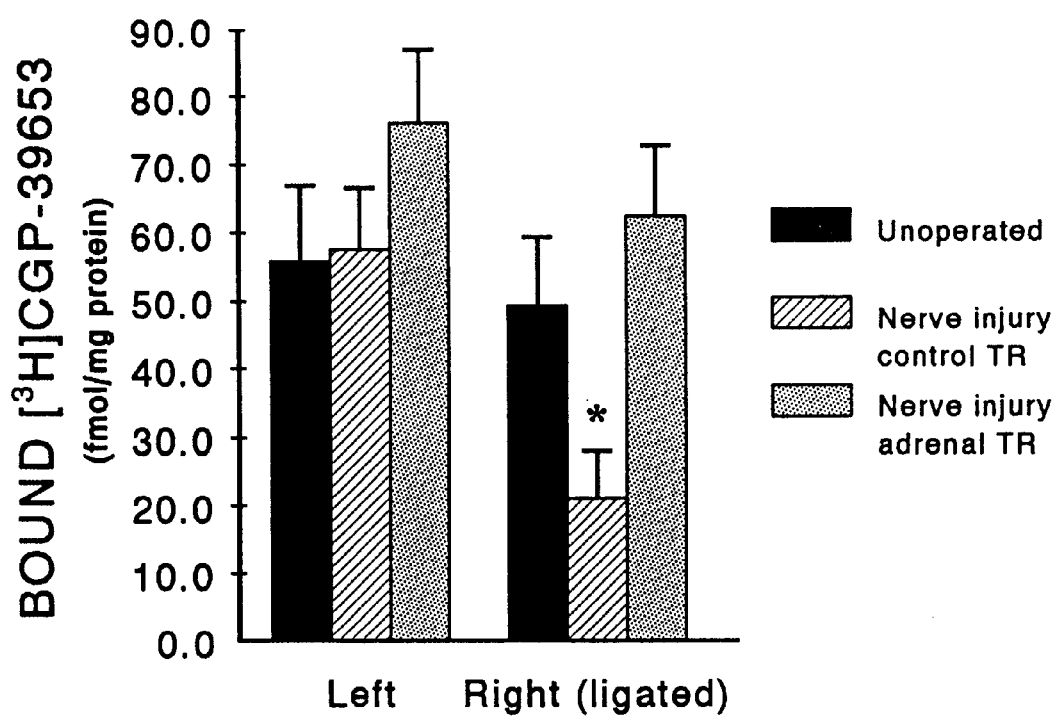
FIG. 9: [$^3$H]CGP-39653 specific binding in spinal cord segments L4–L5 from unoperated control animals (solid bars, n=15), animals with unilateral sciatic nerve constriction injury and control transplants (cross-hatched bars, n=15), and nerve-injured animals with adrenal medullary transplants (stippled bars, n=15). Mean+/−S.E.M. specific binding from the left (contralateral to nerve injury) and right (ipsilateral to nerve injury) segments are shown. For each condition, 5 groups of spinal segments pooled from 3 animals were used. TR=transplant. Asterisk indicates P<0.05 compared to unoperated controls.

Using 10 nM [$^3$H]CGP-39653 in pooled samples of the L4–L5 levels in intact animals, no differences were observed between the left and right sides of the spinal cord (FIG. 9; P>0.05). In contrast, a significant reduction in [$^3$H]CGP-39653 binding ipsilateral to nerve ligation was observed in animals that received control transplants (P<0.05; overall F (df 5,29)=3.83). Binding on the side ipsilateral to nerve injury was reduced to 40.1% of non-ligated control animals, and 35.8% of the side contralateral to nerve injury in these animals. In contrast, in adrenal medullary transplanted animals, binding was restored on the nerve injured side to levels near intact, non-ligated animals. In these animals, slight increases in binding compared to non-ligated animals, particularly apparent on the side contralateral to nerve injury, was observed (44.9%), although this was not statistically significant (P>0.05). [$^3$H]CGP-39653 binding was not different between the nerve-injured and intact sides in adrenal medullary transplanted animals (P>0.05).

IMMUNOCYTOCHEMISTRY

Figure 10A:
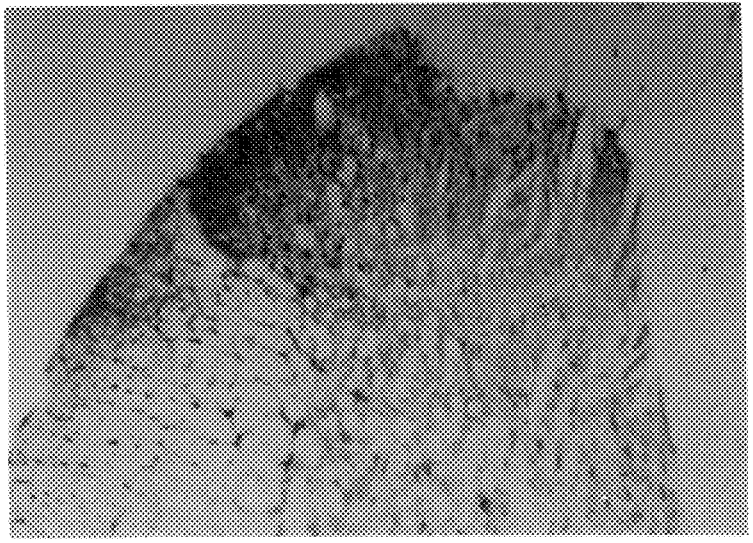
FIG. 10A is taken from an intact, non-ligated animal.
Figure 10B:
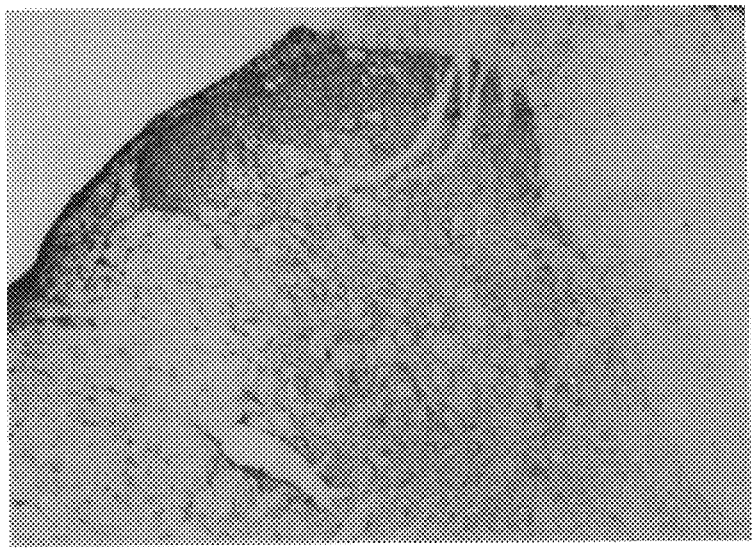
FIG. 10B is taken from an animal with constriction injury of the sciatic nerve and control striated muscle transplant in the spinal subarachnoid space.
Figure 10C:
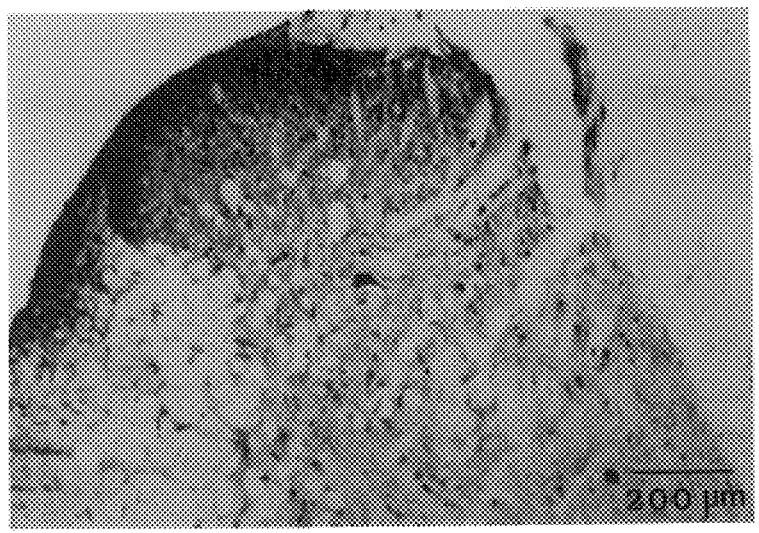
FIG. 10C. is taken from an animal with sciatic nerve ligation and adrenal medullary transplant. Both 10B and 10C show NMDAR1 immunoreactivity 3 weeks following the nerve injury, on the ipsilateral side.
Figure 11A:
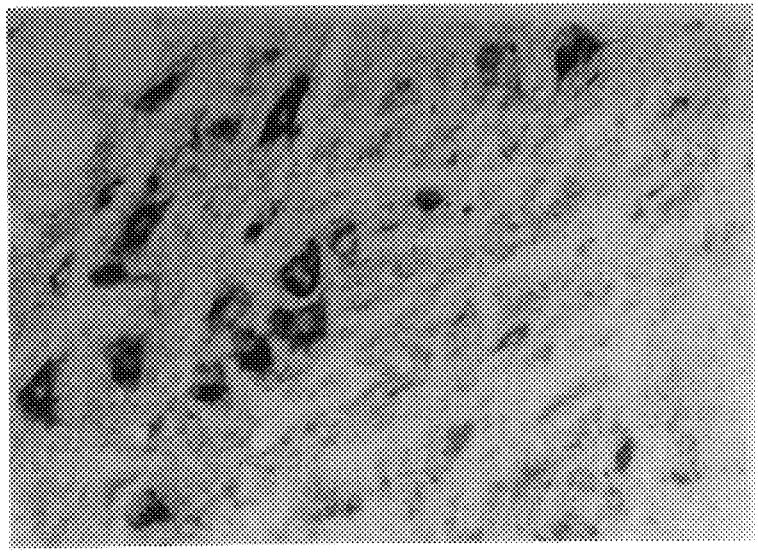
FIG. 11A is taken from an intact, non-ligated animal.
Figure 11B:
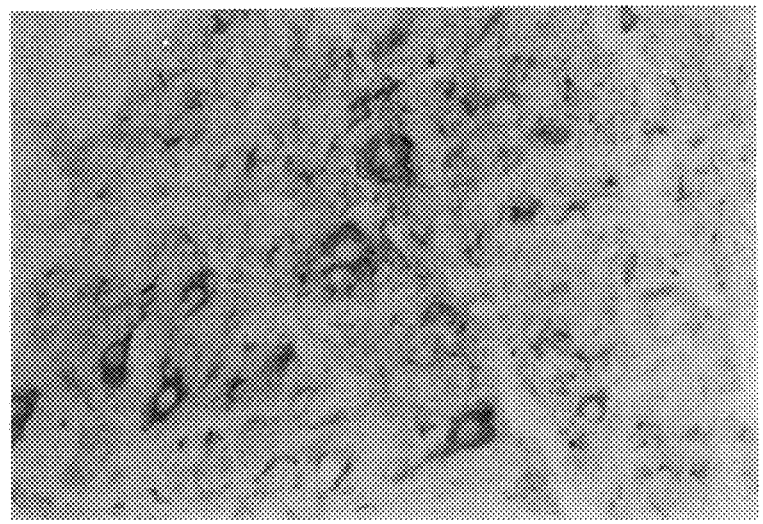
FIG. 11B is taken from an animal with constriction injury of the sciatic nerve and control striated muscle transplant in the spinal subarachnoid space.
Figure 11C:
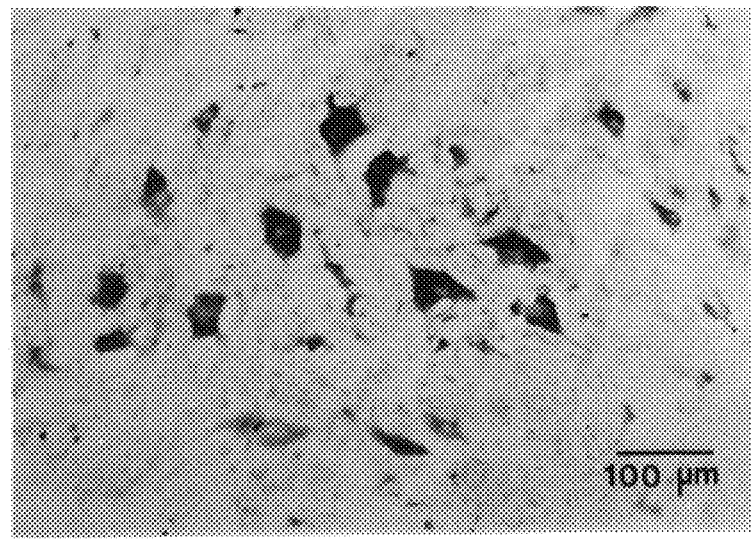
FIG. 11C is taken from an animal with sciatic nerve ligation and adrenal medullary transplant. Both 11B and 11C show NMDAR1 immunoreactivity 3 weeks following the nerve injury, on the ipsilateral side. The large darkly stained neurons in FIG. 11A and 11C are most likely lower motor neurons.

The distribution of NMDAR1 immunoreactivity in dorsal lumbar spinal cord is illustrated in FIG. 10. In intact, non-ligated animals (FIG. 10A), moderate NMDAR1 staining is found throughout the dorsal horn, although it is particularly dense in the superficial laminae (I-II). Staining in these regions appears to be primarily in neural processes, although occasional small stained cell bodies are found. Numerous large cell bodies, most likely motor neurons, were intensely stained in the ventral horn of intact, non-ligated animals (FIG. 11A). This distribution of NMDAR1 staining was similar to that described by others in normal animals [R. S. Petalia et al., Anal. Biochem., 197:220–239 (1980)]. In contrast to intact animals, NMDAR1 staining was markedly reduced in animals with peripheral nerve injury and control transplants on the side ipsilateral to nerve injury. Reduced staining intensity was notable both in the dorsal (FIG. 10B) and ventral (FIG. 11B) gray matter of the spinal cord. In the dorsal horn, the intensity of neuropil staining was low compared to control animals, and stained cell bodies could not be found. In the ventral horn, staining of the motor neurons was quite pale compared to staining in control animals, although the cell bodies appeared to be intact. The densest staining in the ventral horn of ligated animals was in processes found in close proximity to the soma of motor neurons, possibly astrocytic processes. In contrast to nerve injured animals with control transplants, animals that received adrenal medullary transplants showed increased NMDAR1 staining in both the dorsal horn (FIG. 10C) and in ventral horn neurons (FIG. 11C) ipsilateral to nerve injury. In the dorsal horn, staining in the superficial neuropil may be slightly increased compared to non-injured animals (FIG. 10A), although this was not quantified, and cannot be distinguished with certainty from edge artifact. Staining in neuronal cell bodies is also apparent in these animals. In the ventral horn (FIG. 11C), motor neuron staining intensity is markedly increased compared to control transplanted animals (FIG. 11B), and NMDAR1 staining appears restored to that found in intact animals (FIG. 11A).

These findings show that peripheral nerve ligation can have a far reaching effect on the central nervous system. The changes in receptor binding levels are most likely due to either the death of NMDA-receptor containing cells or a generalized down-regulation of the number of NMDA receptors. Either provides strong evidence that there is an increased level of excitatory amino acids present in the spinal cord following peripheral injury. This example also demonstrates the ability of cell transplants to reverse these pathologic changes. The return of normal levels of NMDA-receptors in the spinal cord provides strong evidence that some type of EAA antagonist is working and thus allowing the host's nervous tissue to normalize NMDA receptor levels.

EXAMPLE 4

RESTORATION OF LOST MOTOR FUNCTION
METHODS
PERIPHERAL NERVE INJURY

Adult male Sprague-Dawley rats (Sasco, Inc., WI) weighing 200–250 g at the beginning of the study were used as both hosts and donors. All animal procedures were approved by the Animal Care Committee, University of Illinois at Chicago. Unilateral chronic constriction nerve injury was induced according to methods originally described by Bennett and Xie [G. J. Bennett and Y. K. Xie, Pain, 33:87–107 (1988)]. Animals were anesthetized with sodium pentobarbital (40 mg/kg, i.p., supplemented as necessary), and the right common sciatic nerve was exposed on one side at the mid-thigh level using aseptic surgical techniques. Four 4-0 chromic gut ligatures spaced about 1 mm apart were loosely tied around the sciatic nerve proximal to the trifurcation. No surgery was performed on the left side. Following ligation, the musculature was sutured in layers, and the skin was closed with wound clips. Animals were returned to their cages and food and water were available ad libitum.
ADRENAL MEDULLARY TRANSPLANTS Two weeks following nerve ligation, animals were transplanted with either adrenal medullary or striated muscle (control) tissue in the subarachnoid space of the spinal cord at the level of the lumbar enlargement as described in detail previously [J. Sagen et al., Brain Res., 384:189–194 (1986); J. Sagen et al., Pain, 42:69–79 (1990)]. In addition, an additional group of animals which did not undergo the nerve ligation procedure received adrenal medullary tissue, and an intact control group which did not receive either procedure was included. Another group of animals with nerve ligation did not receive trasnplants. Adrenal medullary tissue for transplantation was obtained from the adrenal glands of adult rats. To prepare adrenal medullary tissue for transplantation, adrenal glands were rapidly removed from donor animals using aseptic techniques. Adrenal medullae were carefully dissected from cortical tissue in ice-cold Hank's buffer under a dissecting microscope, and cut into small pieces (about 0.5 mm$^3$). Medullary tissue from 2 adrenal glands were used. The dorsal surface of the spinal cord was exposed via laminectomy at L1–L3. Tissue pieces were transplanted into the spinal cord subarachnoid space of host animals via a slit in the dura and arachnoid membranes. Control animals received equal volumes of striated muscle tissue. Following transplantation, the musculature was closed in layers and the skin was closed with wound clips.
TESTS OF LOCOMOTOR DYSFUNCTION After a one week recovery period following transplantation, all animals were examined for the appearance of locomotor dysfunction using the following tests:

Table Test (also called the Placing Reflex): The rat is held with hindlimbs slightly lower than forelimbs and the dorsal surface of the hindpaws are brought into contact with the edge of a table and the experimenter records whether there is a relexive placing of the hindpaws on the table surface.

Mesh Test (also called the Grasping Reflex): The rat is placed on a wire grid and the experimenter records whether there is a grasping of the hindpaws to the wire contacting the hindpaws.

Figure 12:
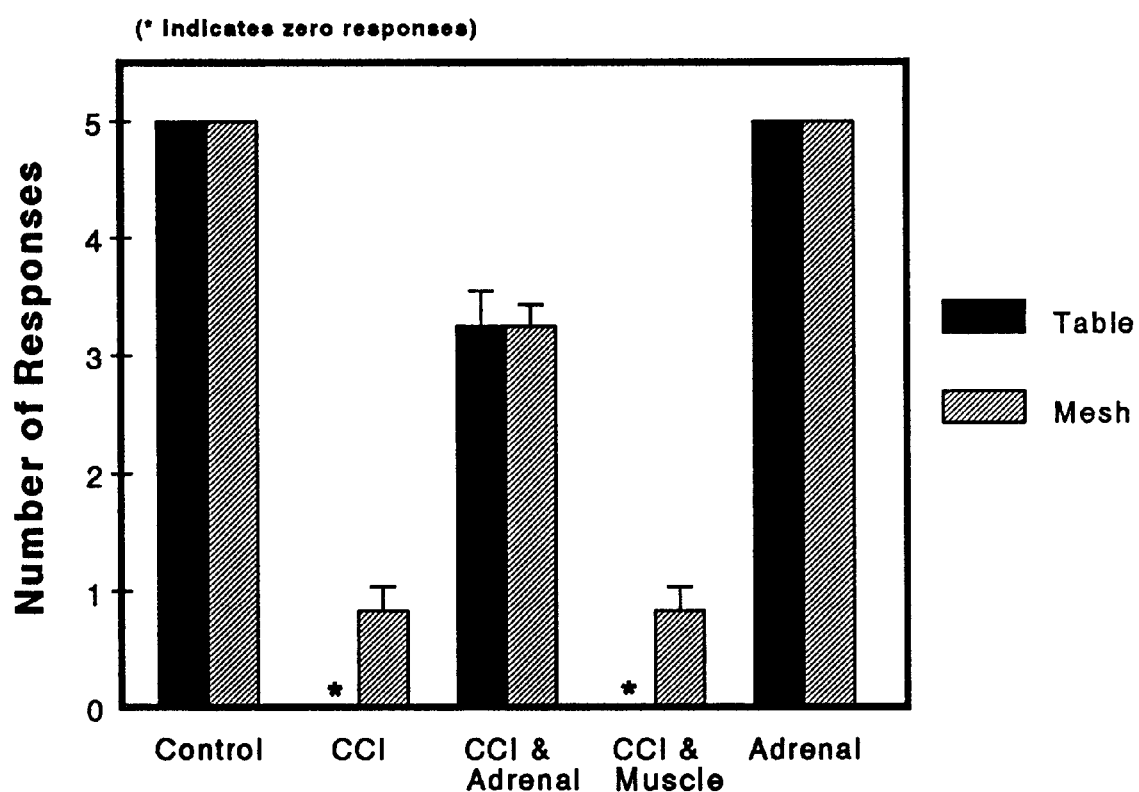
FIG. 12: Changes in motor reflexes following peripheral nerve injury and adrenal medullary grafts. Table test: Number of normal placing reflexes (out of 5 trials) in intact, non-nerve injured animals (control), animals with chronic constricture nerve injury (CCI), animals with CCI and adrenal medullary transplants (CCI & adrenal), animals with CCI and control transplants (CCI & muscle) and animals with adrenal medullary transplants only (no CCI). Mesh test: Number of normal grasping reflexes (out of 5 trials) in the same groups of animals.

Scores for the table test and the mesh test were based on counts of each normal reflex exhibited in 5 trials.
RESULTS In intact control animals, normal placing and grasping reflexes were obtained in 5/5 trials (FIG. 12). The implantation of adrenal medullary tissue in non-nerve injured animals did not alter these normal reflex responses. However, chronic constriction nerve injury severely reduced motor reflexes as assessed by both tests. In particular, no normal placing reflexes were obtained in these animals, and only occasional grasping reflexes were observed. This severe loss in motor reflexes in nerve-injured animals was markedly improved by the transplantion of adrenal medullary tissue in the spinal subarachnoid space (CCI & adrenal), with normal responses obtained 60–70% of the time. No improvement was noted with control transplants. These findings indicate that adrenal medullary transplants can reduce motor dysfunction resulting from peripheral nerve damage. Since peripherial nerve damage is thought to lead to spinal cord dysfunction via excessive EAA release, these findings provide further evidence that EAA-initiated neurotoxicity can be reduced by cellular implants in the CNS.

Thus four examples show many different aspects of the same invention. In Example 1 it was demonstrated that adrenal medullary tissue transplants in the spinal subarachnoid space can reduce behavioral symptoms of hyperalgesia and allodynia induced by NMDA receptor activation. This example, however, did not answer the question of how the transplant was able to produce this effect. Furthermore, this example left open the question as to whether or not isolated cells could produce the same effect. Therefore, in Example 2, it was demonstrated that isolated chromaffin cells also have the ability to act as an EAA antagonist. This example further established that the rest of the support cells in the adrenal medullary tissue were not needed to obtain the EAA antagonistic effect. Finally, this example demonstrated that effects seen in Examples 1, 3 and 4 were the result of substances secreted by the chromaffin cells and not the result of the adrenal tissue reinnervating the host tissue. Thus any cell type which secretes EAA antagonists would work sufficiently well. In Example 3, it was shown that peripheral nerve ligation can have a far reaching effect on the central nervous system. The changes in receptor binding levels were most likely due to either the death of NMDA-receptor containing cells or a generalized down-regulation of the number of NMDA receptors. Either provides strong evidence that there was an increased level of excitatory amino acids present in the spinal cord causing excitotoxic damage. This example also demonstrated the ability of cell transplants to reverse these pathologic changes. The return of normal levels of NMDA-receptors in the spinal cord provides strong evidence that some type of EAA antagonist is working and thus allowing the host's nervous tissue to normalize NMDA receptor levels. Finally, in Example 4, it was shown that cellular implants of cells secreting EAA antagonists can reduce motor dysfunction resulting from peripheral nerve damage. Since peripheral nerve damage is thought to lead to spinal cord dysfunction via excessive EAA release, these findings provide further evidence that EAA-initiated neurotoxicity can be reduced and reversed by cellular implants in the CNS.

It is understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. A method of reducing the severity of excitatory amino acid neurotoxicity resulting from NMDA receptor activation in a subject exhibiting such neurotoxicity comprising the step of administering into a region of the central nervous system of the subject an amount of an adrenal medullary chromaffin cell secretory product effective to provide an NMDA receptor antagonism.

2. The method of claim 1 wherein adrenal medullary cells are implanted into the central nervous system.

3. The method of claim 1 wherein the region of the central nervous system is the subarachnoid space of the spinal cord.

4. The method of claim 1 wherein the excitatory amino acid neurotoxicity is associated with hyperalgesia.

5. The method of claim 1 where in the excitatory amino acid neurotoxicity is the result of a stroke, cerebral ischemia, trauma to the nervous system, or epilepsy.

6. The method of claim 5 wherein the trauma to the nervous system is peripheral nerve damage.

* * * * *